United States Patent [19]

Tamir et al.

[11] Patent Number: 4,883,765
[45] Date of Patent: Nov. 28, 1989

[54] METHOD FOR THE QUANTITATIVE DETERMINATION OF LIPOPROTEIN COMPONENTS IN A BODY FLUID AND METHOD FOR SEPARATING LIPOPROTEINS FROM BLOOD

[75] Inventors: Ilana Tamir, Jerusalem; Ben-Zion Kidron, Givat; Lynn Wang, Gilo; Michael Inbar, Mazkeret Batya, all of Israel

[73] Assignee: I.D.L. Int'l Diagnostic Laboratories Ltd., Jerusalem, Israel

[21] Appl. No.: 91,218

[22] Filed: Aug. 28, 1987

[30] Foreign Application Priority Data

Sep. 4, 1986 [IL] Israel .................................. 79945

[51] Int. Cl.$^4$ ............................................. G01N 33/92
[52] U.S. Cl. .................................. 436/71; 436/16; 436/86; 435/11
[58] Field of Search ............... 436/86, 71, 15, 16, 436/174, 178; 435/11, 19, 25, 28, 4, 29

[56] References Cited

U.S. PATENT DOCUMENTS

| | | | |
|---|---|---|---|
| 4,110,077 | 8/1978 | Klein et al. | 436/71 |
| 4,167,467 | 9/1979 | Golias | 436/71 |
| 4,211,531 | 7/1980 | Das | 436/71 |
| 4,224,031 | 9/1980 | Mee et al. | 436/71 |
| 4,234,317 | 11/1980 | Lucas et al. | 436/71 |
| 4,399,217 | 8/1983 | Holmquist et al. | 436/71 |
| 4,486,531 | 12/1984 | Ziegenhorn et al. | 436/71 |
| 4,503,146 | 5/1985 | Yun et al. | 436/15 |
| 4,565,652 | 1/1986 | Schmidtberger | 530/359 |
| 4,623,628 | 11/1986 | Maaskant et al. | 436/16 |
| 4,656,261 | 4/1987 | Furuyoshi et al. | 530/359 |
| 4,701,418 | 10/1987 | Katopodis | 436/71 |
| 4,743,561 | 5/1988 | Shaffan | 436/71 |
| 4,748,128 | 5/1988 | Katopodis | 436/71 |

FOREIGN PATENT DOCUMENTS 0101764 6/1982 Japan ............................. 436/15

OTHER PUBLICATIONS

"Calibrator Comp Based Upon Dialyzed Blood" Research Disclosure (Nov. 1978) No. 175.
"Rubella Serology: a Comparison of Four Methods for Exclusion of Nonspecific Serum Inhibitors", T. Traavi, O. Spanne and S. Mennen, J. Hyg. Camb. (1981), 86, 315, printed in Great Britain, pp. 315–327.
"The Isolation of Alpha-1-Protease Inhibitor by a Unique Procedure Designed for Industrial Application", Charles B. Glaser, Mario Chamoro, Robert Crowley, Lucy Karic, Anne Childs, and Minerva Calderon, Institutes of Medical Sciences, 2200 Webster Street, San Francisco, CA 94115, Analytical Biochemistry 124, 364–371 (1982), pp. 364–371.
"The Use of Polyethylene Glycol Precipitation to Detect Low-Avidity Anti-DNA Antibodies in Systemic Lupus Erythematosus", Ruud Smeenk and Lucien Aarden, Department of Autoimmune Diseases, Central Laboratory of the Netherlands Red Cross Blood Transfusion Service, and Laboratory for Experimental and Clinical Immunology, University of Amsterdam, Amsterdam, the Netherlands, Journal of Immunological Methods, 39 (1980) 165–180.
"Evaluation of Four Reagents for Delipidation of Serum", S. T. Agnese, F. W. Spierto, and W. Harry Hannon, the Centers for Disease Control, Public Health Service, Department of Health and Human Services, Atlanta GA 30333, pp. 98–100.

*Primary Examiner*—David L. Lacey
*Assistant Examiner*—L. Johnson
*Attorney, Agent, or Firm*—Browdy and Neimark

[57] ABSTRACT

A method, device and kit for the quantitative determination of lipoprotein components, especially cholesterol and triglycerides, in body fluids, especially human serum, plasma or whole blood utilizing the selective adsorption of lipoproteins on particulate silica. This selective adsorption is also useful for the quantitative separation of lipoproteins from samples of whole blood for diagnostic purposes.

10 Claims, 6 Drawing Sheets

METHOD FOR THE QUANTITATIVE DETERMINATION OF LIPOPROTEIN COMPONENTS IN A BODY FLUID AND METHOD FOR SEPARATING LIPOPROTEINS FROM BLOOD

This invention relates to a method and test kit for the quantitative determination of lipoprotein components, especially cholesterol and triglycerides, in body fluids, especially human serum, plasma or whole blood. The invention further relates to a method for the quantitative separation of lipoproteins from samples of whole blood, for diagnostic purposes.

The term "lipoprotein component" as used herein is meant to refer to any of the substances making up the lipoproteins in the body fluids, in particular all forms of serum cholesterol (HDL, LDL and VLDL), triglycerides and apolipoproteins.

Practically all of the hitherto conventional methods for the quantitative determination of cholesterol and triglycerides are based on enzymatic or chemical color reactions and spectrophotometric determination of the optical density of the reaction mixture at a suitable wavelength. Since turbid or colored biological liquids, such as blood, interfere with such spectrophotometric measurements, the conventional tests for cholesterol and triglycerides must be carried out with plasma or serum from which the red blood cells have been separated. Furthermore, since a significant quantity of cholesterol is incorporated into the membrane of red blood cells, and this incorporated cholesterol is not relevant to the measurement of total serum or plasma cholesterol levels for diagnostic purposes, it is necessary to separate out the red blood cells from the sample without releasing the cholesterol of the red blood cell membranes.

The normal and most conventional manner of separating serum or plasma from erythrocytes is by centrifugation. This requires comparatively large blood samples for the centrifugation and for carrying out the aforesaid test and to this end blood must be drawn, as a rule, from a vein, an operation which is restricted to qualified medical or para-medical personnel. A further drawback is that this test procedure requires comparatively expensive apparatus, in particular a centrifuge.

There exists a growing general need for simple, rapid and reliable methods of diagnostic testing, including determinations of components of blood lipoproteins, such as cholesterol and triglycerides, which can be carried out in doctors' offices and even in patients' homes. Clearly, the hitherto conventional methods for performing such tests are unsuitable for this purpose. It is one object of the present invention to satisfy the aforesaid need, i.e. to provide the private medical practitioner or the patient with a simple and reliable method for the determination of lipoprotein components, e.g. total cholesterol or triglycerides in the blood, which method requires a comparatively very small sample of whole blood, yet is applicable to other body fluids, in particular plasma or serum.

It is a further object of the present invention to provide a test kit adapted for the rapid and easy performance of the diagnostic method of the present invention.

Yet another object of the present invention is to provide a novel method for the quantitative separation of lipoproteins from a sample of whole blood, for diagnostic purposes.

The present invention, in accordance with one aspect thereof, provides a method for the quantitative determination of a lipoprotein component in a sample of a body fluid, which method comprises:

(a) contacting said sample with a quantity of particulate silica which is capable of selectively adsorbing the entire amount of lipoproteins in said sample;

(b) separating the non-adsorbed components of the sample from the silica with the said lipoproteins adsorbed thereon; and (c) quantitatively determining said lipoprotein component.

The separation of the non-adsorbed components of the sample from the silica, in step (b) of the above method may comprise physical separation of the silica from the liquid sample and washing the silica with water or a suitable aqueous solution (e.g., saline or a buffer solution) so as to free it from residual liquid sample adhering thereto. While in principle said physical separation may be done by centrifugation, it is more simply and efficiently effected in accordance with a preferred embodiment of the invention wherein the particulate silica is permanently attached to a solid, inert carrier of suitable shape and size, e.g. a glass or plastic rod or plate coated with a layer of particulate silica, hereinafter referred to as a "test device" or briefly "device".

In accordance with another preferred embodiment of the invention, especially adapted to very small sample volumes, the particulate silica is employed in an amount sufficient to absorb the entire sample. In accordance with such a procedure, the separation in step (b) above can be simply and effectively achieved by washing the silica with water or a suitable aqueous solution.

Thus, in accordance with the above preferred embodiment, the invention provides a method for the quantitative determination of a lipoprotein component in a sample of a body fluid, said method comprising:

(a) contacting said sample with particulate silica capable of selectively adsorbing the entire lipoproteins in said sample, the amount of said silica being sufficient to absorb the entire sample;

(b) separating the non-adsorbed components of the sample from the adsorbed lipoproteins by washing the silica with water or an aqueous solution;

(c) incubating the silica with a conventional reagent solution for determining said lipoprotein component by an enzymatic-colorimetric reaction;

(d) removing the silica from the liquid incubation mixture; and (e) evaluating the intensity of the color generated in said liquid mixture by said enzymatic-colorimetric reaction and comparing the intensity value with one or more standards of said lipoprotein component.

Where the body fluid is whole blood, the color intensity values obtained by the method of determination according to the invention, should advantageously be corrected for hematocrit (in the blood tested). Thereby the results can be expressed in concentrations of the lipid component in plasma and a closer correlation can be achieved with values obtained by conventional methods of determination (using samples of plasma). Preferably, the particulate silica employed in the above method is comprised in a test device as described hereinabove.

The particulate silica suitable for use in the methods and devices of the present invention should be of such microstructure and chemical composition as to selectively adsorb the lipoporteins present in body fluids. Among the very large choice of available silica types and grades, those fulfilling the above requirement can be selected empirically by simple and straightforward tests. It has been found that fumed silica is most suitable for use in accordance with the present invention.

Fumed silica is an extremely pure silicon dioxide of amorphous structure which is produced from $SiCl_4$ by a flame hydrolysis process with hydrogen-oxygen gas mixture. This process yields a highly dispersed silica with controlled particle size and chemical constitution. It is commercially available in various grades from different manufacturers under various trade names, e.g. "Aerosil" (Degussa Company).

Fumed silica was known to strongly and selectively adsorb lipoproteins and was thus used, inter alia, for the removal of the lipoproteins from samples of human plasma and serum. (c.f., e.g. Traavik T., O. Spanne & S. Mennen, "Rubella serology: a comparison of four methods for exclusion of non-specific serum inhibitors", J. Hyg. Camb. 86:315 (1981); Smeek R. and L. Aarden T, "The use of polyethylene glycol precipitation to detect low-avidity anti-DNA antibodies in systemic lupus erythematosus", J. Imm. Methods 39:165-180 (1980); S. T. Agnese, F. W. Spierto and W. H. Hannon, "Evaluation of four reagents for delipidation of serum", Clin. Biochem. 16:98-100 (1983); and Glaser et al., "The isolation of alpha-1-protease inhibitor by a unique procedure designed for industrial application", Anal. Biochem. 1246:364-371 (1982)). However, none of these investigators described the application of fumed silica for the removal of lipoproteins from whole blood, nor did they describe the use of the lipoproteins adsorbed on the fumed silica for any purpose, a fortiori for the quantitative determination of lipoprotein components in the original plasma or serum sample.

It has been surprisingly found in accordance with the present invention that lipoproteins are so strongly retained by the silica on which they are selectively adsorbed, as to withstand thorough washing with water or other aqueous solution, thereby enabling the complete removal from the silica of the non-adsorbed components of the plasma or blood, in particular the red blood cells.

Based on the above findings, the present invention in accordance with another aspect thereof, provides a method for the quantitative separation of lipoproteins from a sample of whole blood, which comprises:

(a) contacting said sample with a solid phase comprising a quantity of particulate silica which is capable of selectively adsorbing the entire amount of lipoproteins in said sample;

(b) separating said solid phase with said lipoproteins adsorbed thereon from the non-adsorbed components of the sample;

(c) washing said solid phase with water or an aqueous solution.

In the above method of separation, the solid phase preferably consists of a device of the type described hereinabove.

It has further been found in accordance with the invention that, notwithstanding said high affinity of the silica for lipoproteins, it is possible to release lipoprotein components, e.g. cholesterol and triglycerides, from the silica and to determine them by enzymatic or chemical color reactions, by incubating the silica with these components adsorbed thereon in a suitable reagent solution of the type conventionally used for determining cholesterol or triglycerides, owing to the presence in such reagent solutions of certain enzymes and conventional surfactants. Reagent solutions of this type were disclosed, e.g. by Trinder, P., Ann. Clin. Biochem. 6:24 (1969); Allain, C. C. et al., Clin. Chem. 20:470 (1974); and Fossati, F. and Prencipe, L., Clin. Chem. 28: 2077-80 (1982).

The intensity of the color generated by the color reaction with the cholesterol or the triglyerides is preferably and most accuratedly evaluated spectrophotometrically by measuring the optical density of the solution at a specific wavelength. The invention does not preclude, however, any other possible manner of color intensity evaluation, including visual comparison with a set of standards.

Clearly, before carrying out the spectrophotometrical measurement of the optical density of the solution obtained by the abovementioned enzymatic or chemical color reaction, the depleted silica must be removed from the solution which is to be measured, and this is most simply and efficiently effected when a test device according to the above described preferred embodiment of the invention is used.

The test procedure in accordance with the abovementioned preferred embodiment of the invention may be exemplified by the use of a glass or plastic slide coated with a layer of fumed silica to determine total serum cholesterol in a sample of whole human blood. The entire whole blood sample, say 5 $\mu$l or less, is applied to the surface of the coated slide and is entirely absorbed by the layer of fumed silica. After incubation for several minutes, the coated slide is thoroughly washed by holding it under a stream of tap water (or with distilled or deionized water), thereby removing from the fumed silica all red blood cells and other non-adsorbed components of the sample. The slide is thereafter immersed in a suitable reagent solution for the enzymatic determination of total cholesterol, contained in a test cuvette. The reagent solution with the slide immersed therein is incubated, e.g. at 37° C., for the required length of time, say 25 minutes. The slide is then removed from the cuvette and the optical density of the resulting solution is measured at 516 nm. The concentration of cholesterol in the sample is then calculated by comparing the value of the optical density thus measured, preferably after correcting them for hematocrit, with a calibration curve plotted from values measured in standard solutions containing different known concentrations of cholesterol or by another standardization method.

The determination of triglycerides in accordance with the invention can be carried out in the same manner as described above, the only difference being the reagent solution comprising the enzymes and surfactants, in which the test device is immersed and incubated.

It should be noted, however, that the determination methods of the present invention are not limited to the above described preferred embodiment, wherein a test device is employed, and it is also possible to contact the sample of the body fluid with particulate silica in dispersed form. In such a case, and especially when a sample of whole blood is employed, one or more centrifugation operations will be needed, e.g. to separate the particulate silica from red blood cells and/or other non-adsorbed components of the sample after the washing stage and, possibly, to separate the particulate silica from the incubation mixture (with the enzymatic or chemical reagent solution) before the spectrophotometrical determination. Notwithstanding the need for centrifugation, the last mentioned more general embodiment of the invention is advantageous, as compared to hitherto known determination methods, in that it requires considerably smaller blood samples obviating the need to draw the blood from a vein.

In accordance with another aspect of the invention there is provided a test kit for the quantitative determination of a lipoprotein component in a sample of a body fluid, which kit comprises:

(i) at least one packaged, predetermined amount of silica capable of selectively adsorbing the entire amount of lipoprotein components in said sample;

(ii) packaged reagent solution for the enzymatic-colorimetric determination of said lipoprotein component, or packaged lyophilized reagent mixture for reconstituting said solution in situ; and (iii) at least one packaged standard solution containing a known concentration of said lipoprotein component.

In a preferred test kit in accordance with this embodiment of the invention, constituent (i) above is in the form of a test device consisting of silica, preferably fumed silica, permanently attached to a solid, inert carrier.

A test kit according to the invention may comprise, as constituent (ii) above, a reagent solution (or a lyophilized reagent mixture) for the determination of either the total cholesterol or the triglycerides in the sample. Alternatively, a combined test kit may include two such reagent solutions or lyophilized mixtures for determining each of the aforesaid components of the sample. Where the test kit according to the invention comprises a lyophilized reagent mixture, it may preferably further comprise packaged aqueous solution, e.g. a buffer solution, for reconstituting the reagent solution from said lyophilized mixture.

The invention will now be further illustrated in detail in the following non-limiting examples and with the aid of the accompanying drawings in which.

EXAMPLE 1

Figure 1:
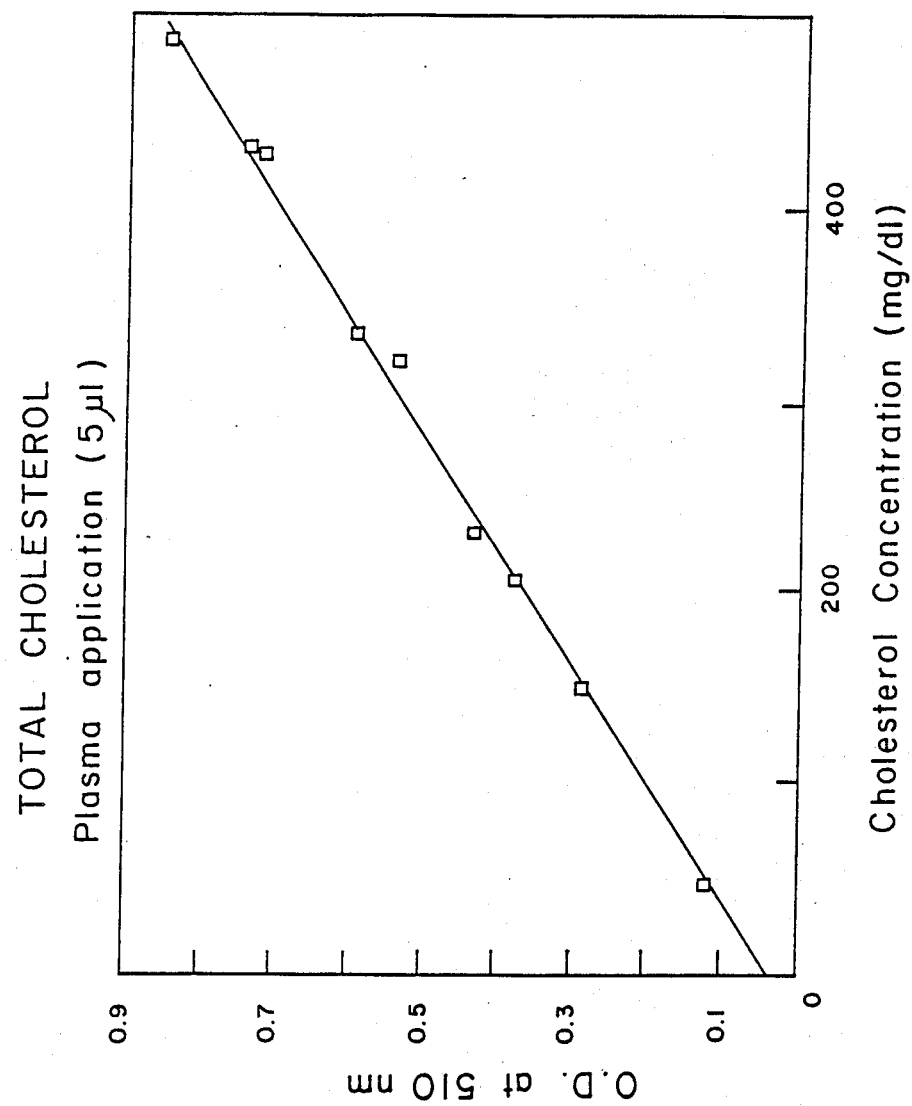
FIG. 1 is a graphical representation of the correlation between the optical density of various plasma samples (determined by use of a test device by the procedure described in Example 5A herein) and the concentration of total cholesterol in said samples (determined by conventional methods).

Determination of Cholesterol in Human Plasma (Particulate Fumed Silica)

Each of seven 25 $\mu l$ samples of human plasma was diluted by 175 $\mu l$ of water and the resulting solutions were introduced into microtest tubes each containing 5 mg of highly adsorbent silica (Aerosil 380 or Aerosil 200). The mixtures were incubated for 5 minutes at room temperature. The Aerosil was washed twice with 250 $\mu l$ portions of water and the Aerosil collected by centrifugation for 10 minutes at 3,000 rpm. Each of the thus obtained Aerosil phases and each of the supernatant solutions were then tested for the presence of cholesterol by a modification of the test procedure for the determination of total cholesterol described in Allain, C. C. et al., Clin. Chem. 20:470 (1974). This was done by incubation of each Aerosil phase, or of 20 ul of each supernatant solution with 2 ml of a reagent solution containing per 100 ml:

| | |
|---|---|
| Horseradish peroxidase | 500 U |
| Cholesterol oxidase | 10 U |
| Cholesterol esterase | 37.5 U |
| Sodium cholate | 3.85 g |
| 3,5-Dichloro-2-hydroxybenzenesulfonic acid | 4.03 g |
| 4-amino-antipyrine | 0.036 g |
| Triton X-100 | 0.64 ml |

Triton X-100 is a surface wetting agent which is formed as a condensation product of ethylene oxide and an alkyl phenol.

The mixtures were incubated at 37° C. for 25 minutes and thereafter their optical density was measured at 516 nm.

No cholesterol could be detected in any of the supernatant samples and the results obtained with the Aerosil samples are summarized in the following Table I:

TABLE I

| Aerosil Type | Sample No. | No. Replicates | Cholesterol by Conventional Test mg/dl | Cholesterol Determined According to Example 1 | | Cholesterol Recovery % |
|---|---|---|---|---|---|---|
| | | | | mg/dl | C.V. | |
| 380 | 1 | 7 | 305.1 | 250.1 | 5.832 | 82.0 |
| " | 2 | 9 | 269.3 | 240.2 | 4.792 | 89.2 |
| " | 3 | 6 | 245.3 | 207.9 | 4.632 | 84.7 |
| " | 4 | 8 | 141.7 | 132.2 | 3.085 | 93.3 |
| " | 5 | 8 | 72.5 | 62.8 | 5.035 | 86.6 |
| " | 6 | 7 | 299.5 | 237.8 | 13.336 | 79.4 |
| " | 7 | 9 | 74.4 | 54.4 | 13.240 | 73.1 |

TABLE I-continued

| Aerosil Type | Sample No. | No. Replicates | Cholesterol by Conventional Test mg/dl | Cholesterol Determined According to Example 1 mg/dl | C.V. | Cholesterol Recovery % |
|---|---|---|---|---|---|---|
| 200 | 8 | 3 | 151.2 | 147.9 | | 97.8 |
| " | 9 | 3 | 136.4 | 130.2 | | 95.4 |
| " | 10 | 3 | 258.5 | 229.8 | | 88.9 |
| " | 11 | 3 | 141.7 | 139.9 | | 98.7 |
| " | 12 | 3 | 269.3 | 239.9 | | 91.1 |
| " | 13 | 3 | 196.4 | 187.1 | | 95.3 |

EXAMPLE 2

Determination of Triglycerides in a Plasma Sample (Particulate Fumed Silica)

The procedure of Example 1 was repeated except that a suitable conventional test solution for the determinatin of triglycerides was used.

This reagent contained the following ingredients:

| | |
|---|---|
| Phosphate buffer (pH 7.2) | 50 mmol/L |
| Lipoproteinlipase | 15 U/ml |
| Glycerolkinase | 0.05 U/ml |
| Glycerolphosphate oxidase | 3.5 U/ml |
| Peroxidase | 0.5 U/ml |
| ATP | 0.7 mmol/L |
| 4-Aminophenazone | 0.3 mmol/L |
| Potassium ferrocyanide | 3.0 μmol/L |
| Magnesium salts | 0.6 mmol/L |
| 3,5-Dichloro-2-hydroxybenzenesulfonic acid | 1.7 mmol/L |
| Triton X-100 | 0.1 ml/L |

No triglycerides could be detected in the supernatant samples and the results obtained with the Aerosil samples are summarized in the following Table II:

TABLE II

| Aerosil Type | Sample No. | O.D. by Conventional Test | O.D. According to Example 2 | TG Recovery % |
|---|---|---|---|---|
| 200 | 1 | 1.958 | 1.810 | 92.4 |
| " | 2 | 1.174 | 1.131 | 96.3 |
| " | 3 | 2.345 | 2.234 | 95.3 |
| 380 | 1 | 1.958 | 1.612 | 82.3 |
| " | 2 | 1.174 | 1.099 | 93.6 |
| " | 3 | 2.345 | 2.332 | 99.4 |

EXAMPLE 3

Determination of Total Cholesterol in Whole Human Blood (Particulate Fumed Silica)

The procedure of Example 1 was repeated with Aerosil 380, except that a sample of whole human blood instead of plasma was used and that three more washes with 250 μl portions of water were necessary in order to remove all the red blood cells from the Aerosil phase. A slight red color remained in the last wash solution and this was used as a blank in the spectrophotometric determination. In this procedure 92% of the total cholesterol of the blood sample were detected (as compared to the results of a conventional total cholesterol determination carried out with plasma from the same blood sample).

EXAMPLE 4

Preparation of Test Device (Glass Slides Coated With Aerosil 380)

A. A thin layer of sodium silicate - water glass (Bio-Lab) was applied by means of a brush to both sides of glass (dimensions 30×8×3 mm) and the slides were then pressed into a pile of Aerosil 380 (Degussa). The Aerosil adhered to the slides and these coated glass slides were baked at 90° C. fir 18 hours. After cooling to room temperature, the excess Aerosil was removed from the coated slides by an air jet.

B. A second layer of Aerosil 380 was created by the method described in 4(A) above, since previous studies had indicated that this second Aerosil layer had a larger surface area and a more uniform distribution, resulting in a higher recovery of cholesterol by the device.

C. The slides doubly-coated with Aerosil 380 were incubated for 18 hours in glacial acetic acid in order to reduce the high pH value (ca. 11-12) of the water glass. The salts and the excess acetic acid were removed by an intensive washing with a stream of tap water and then with deionized water. Introduction of such a slide into distilled water resulted in a pH of 5-6 of the aqueous phase.

EXAMPLE 5

Determinatin of Total Cholesterol in Plasma and in Whole Blood Using Test Device (Glass Slides Doubly-Coated with Aerosil 380)

In th following series of determination of total cholesterol in plasma and in whole blood, glass slides coated twice with Aerosil 380, as described in Example 4, were employed.

A. The Aerosil-coated slides were dipped in saline and excess saline was removed by touching the edge of the slide to absorbent paper. Following this, 5 μl from various plasma samples were applied on both sides of the slides, distributed in several spots. The slide was then left for 5 minutes and washed under a stream of tap water for 30 seconds, whereby all the substances that were not adsorbed to the Aerosil were removed. These slides were then introduced each into a cuvette containing 1 ml of a reagent solution consisting of detergents, enzymes and substrates for the determination of cholesterol. The reagent contained the following materials:

| | | |
|---|---|---|
| Cholesterol oxidase | 0.48 | U/ml |
| Cholesterol esterase | 1.68 | U/ml |
| Horseradish peroxidase | 3.00 | U/ml |
| 3,5-Dichloro-2-hydroxybenzenesulfonic acid | 0.02 | mmol/ml |
| Sodium cholate | 0.006 | mmol/ml |
| 4-amino-antipyrine | 0.0005 | mmol/ml |
| Triton X-100 | 0.0064 | ml/ml |
| 0.1 M phosphate buffer | to 1.0 | ml |

(KH₂PO₄) pH 6.6

The slides were incubated in this reagent solution for 45 minutes at 37° C. The slide were then removed and the optical densities of the solutions were measured at 516 nm. The results are summarized in the linear graph shown in FIG. 1.

Figure 2:
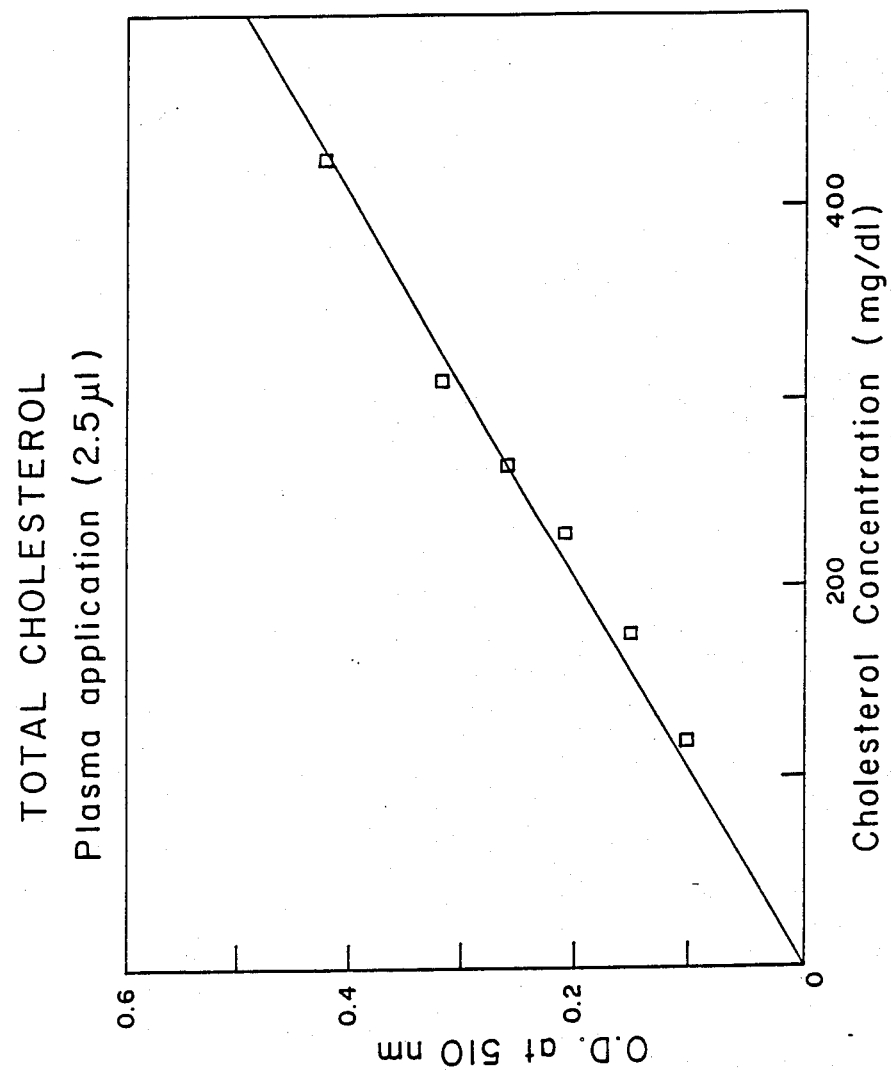
FIG. 2 is a graphical representation of the correlation between optical densities of diluted plasma samples (1:1 with PCS) determined by the procedure described in Example 5B herein and total cholesterol concentrations determined by conventional methods.

B. The procedure described in 5(A) above was repeated except that the plasma samples were diluted from a single plasma sample to give samples with decreasing concentrations of cholesterol and each dilution was diluted with an equal volume (1:1) of PCS (plasma converted serum) to simulate whole blood containing red blood cells. 5 μl samples of each dilution, corresponding to 2.5 μl of undiluted plasma samples, were applied to Aerosil 380-coated slides. The results are summarized graphically in FIG. 2.

C. The procedure described in 5(A) above was repeated except thet 5 μl samples of whole blood rather than plasma were applied to the test device, and therefore the substances removed by the 30 second washing procedure included red blood cells and hemoglobin. In addition, the hematocrit values were measured and used to correct the 5 μl whole blood sample to correspond to 2.5 μl of plasma.

Figure 3:
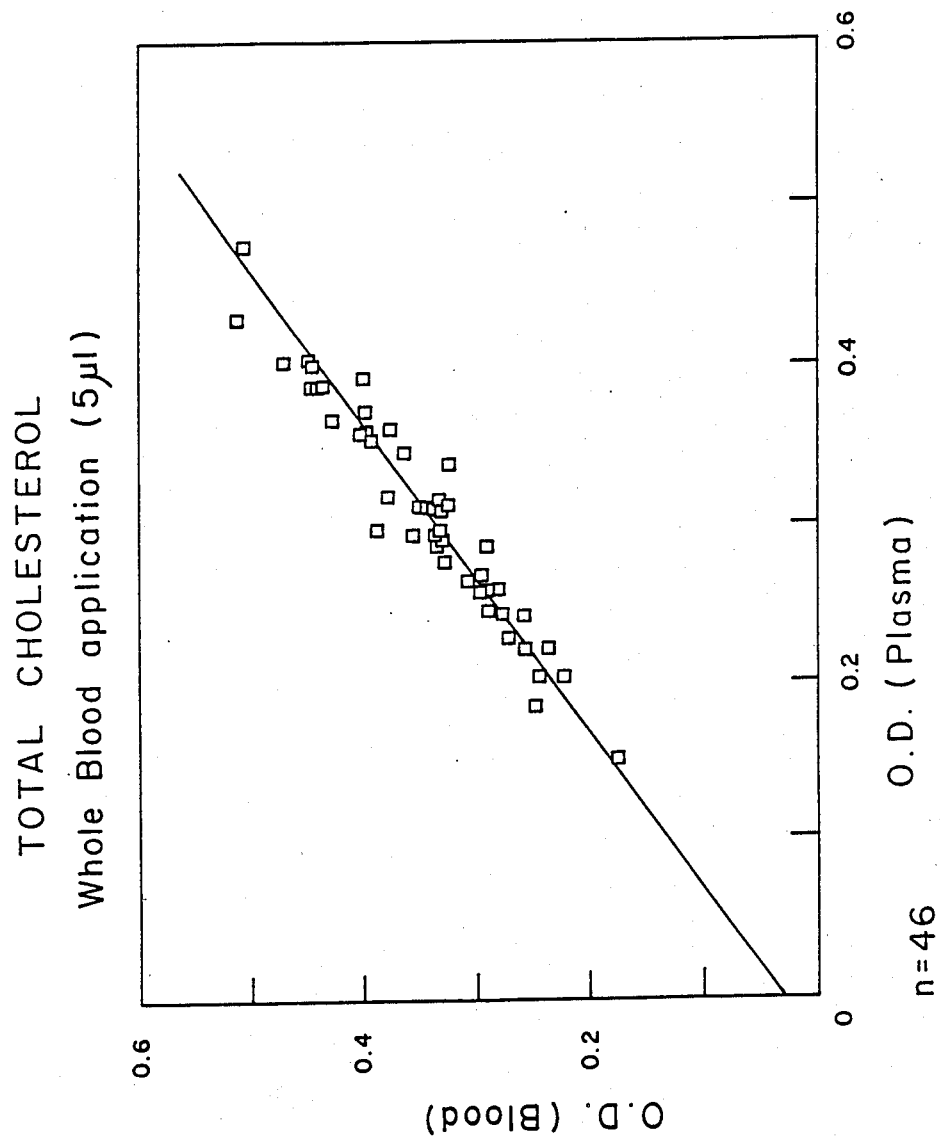
FIG. 3 is a correlation curve between optical density values, before the correction for hematocrit, obtained by total cholesterol determination in whole blood samples with a test device according to the invention by the procedure described in Example 5C herein, and optical density values obtained from corresponding sample of plasma by the conventional method.
Figure 4:
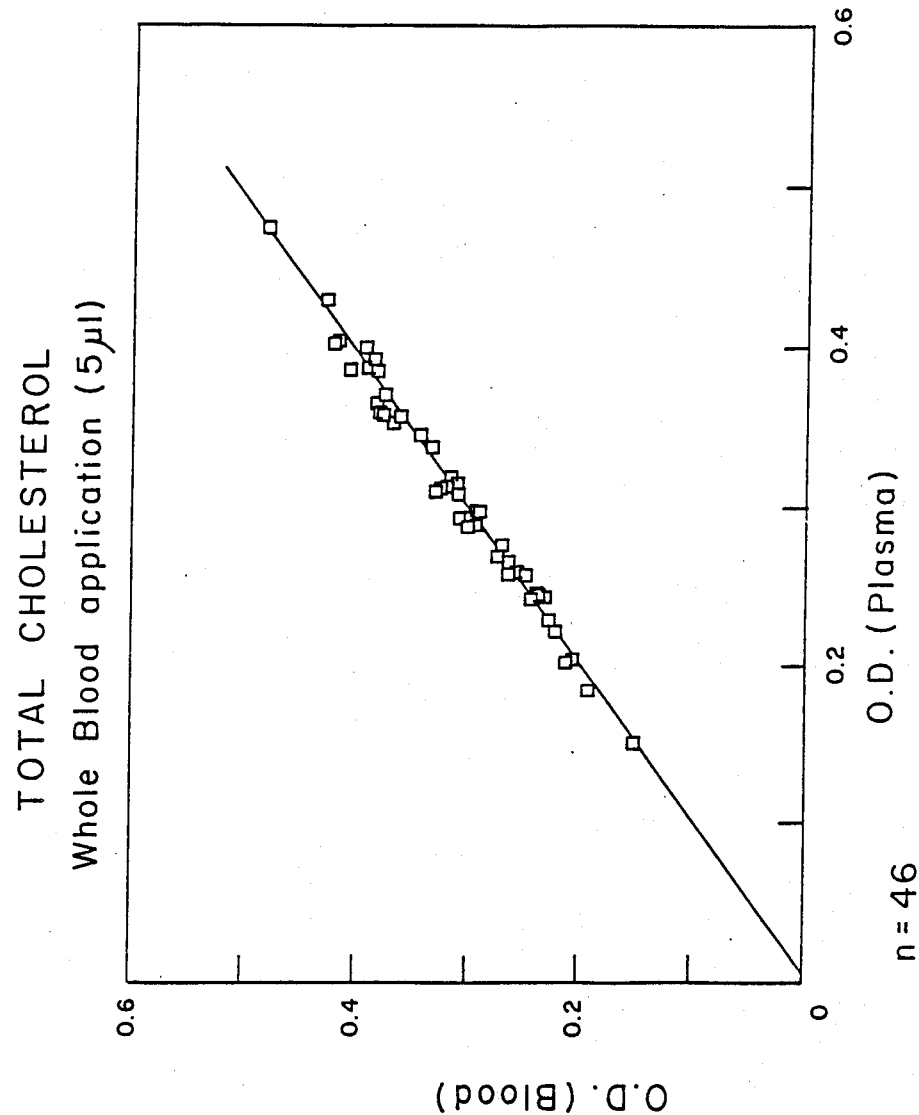
FIG. 4 is a correlation curve corresponding to that of FIG. 3 (determination of total cholesterol in whole blood with a test device according to the invention by the procedure described in Example 5C herein), after the correction for hematocrit.
Figure 5:
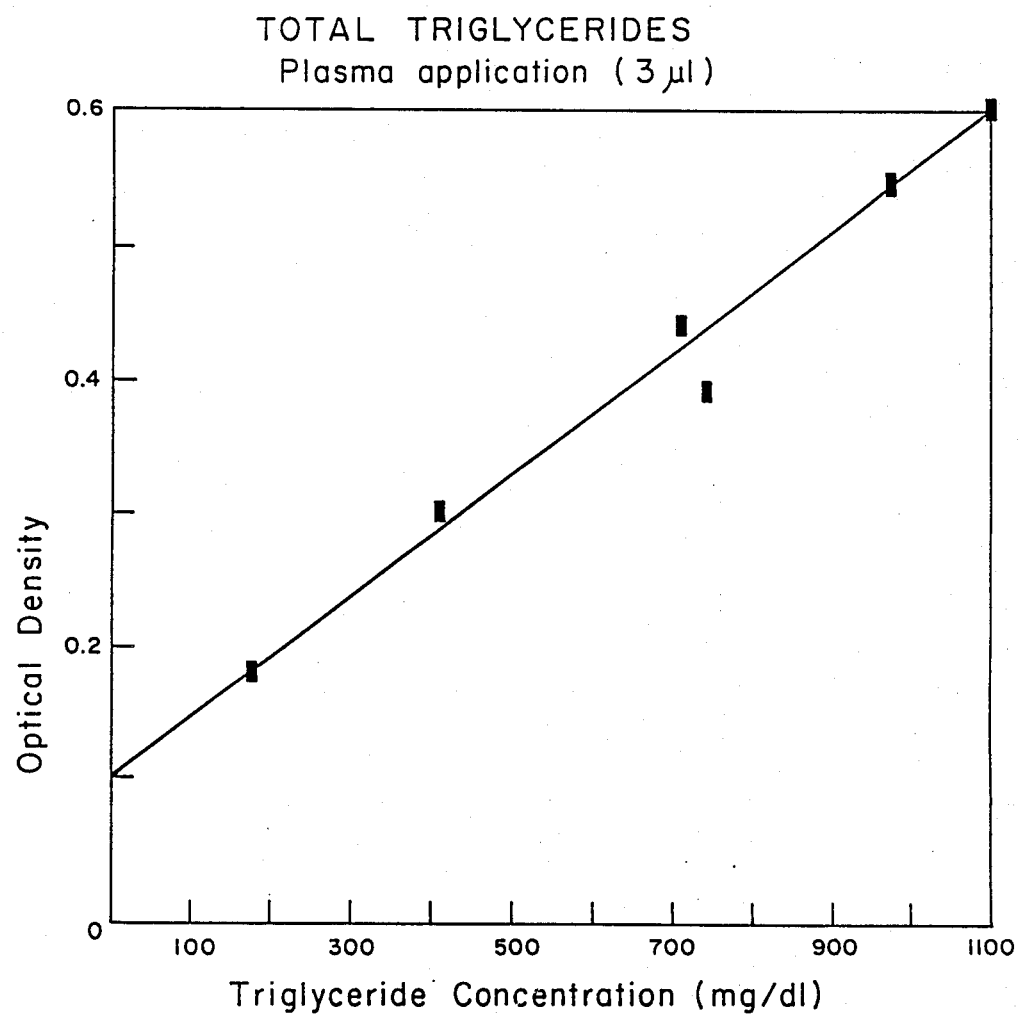
FIG. 5 is a correlation curve between the optical densities obtained by determinations of total triglycerides in 3 $\mu l$ plasma smaples with a test device according to the invention as described in Example 6A herein, and the total triglycerides concentrations as determined by conventional methods.
Figure 6:
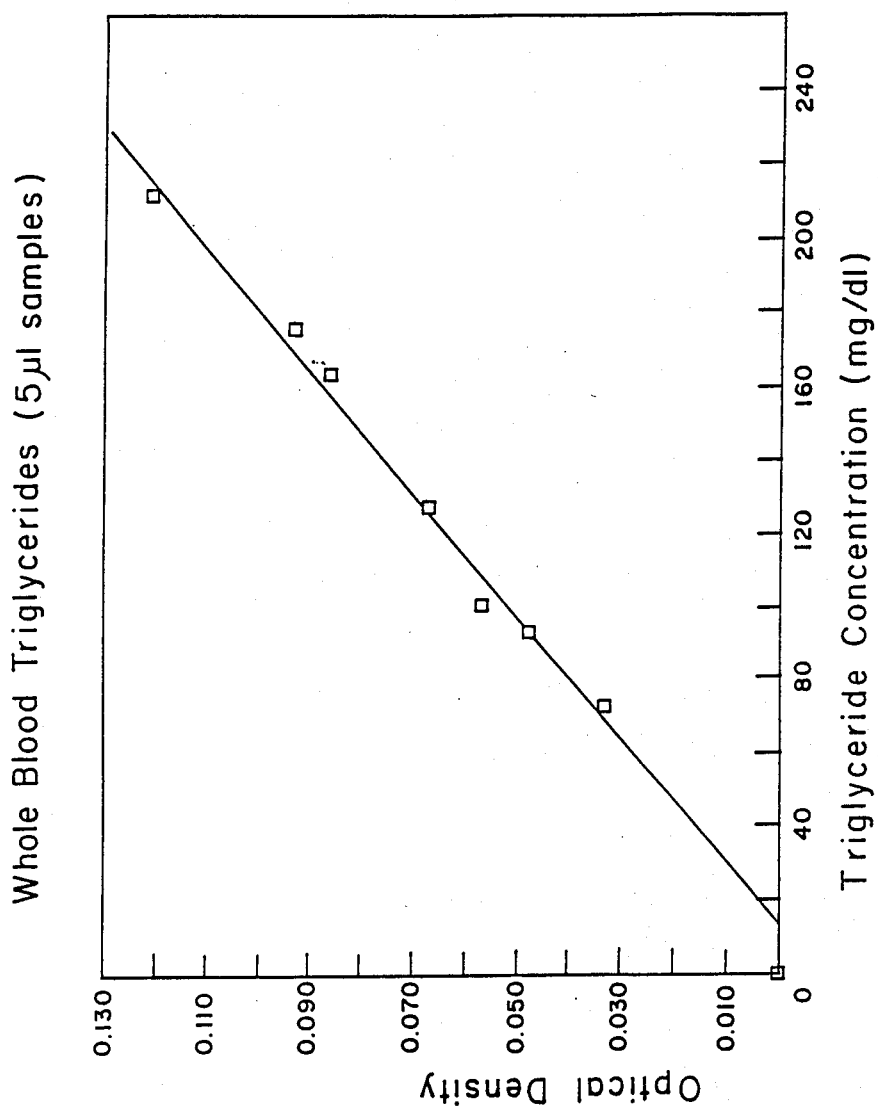
FIG. 6 is a correlation curve similar to that of FIG. 5 except that the total triglycerides were determined in 5 $\mu l$ samples of whole blood by the procedure described in Example 6B herein and the results were corrected for hematocrit.

The results are shown in FIGS. 3 and 4. The effect of the hematocrit correction may be seen by comparing FIG. 3 vs. FIG. 4, where the correction for the hematocrit was 5.3%.

The total number of samples was 46 and the correlation factor (with results determined in plasma by conventional methods) was 96.6% without hematocrit correction and 99.3% with hematocrit correction.

EXAMPLE 6

Determination of Total Triglycerides in Plasma and in Whole Blood Using Test Device (Glass Slides Doubly-Coated With Aerosil 380))

In the following determinations of total triglyceride in plasma and in whole blood, glass slides coated twice with Aerosil 380, as described in Example 4, were employed.

A. The procedure described in Example 5(A) was repeated except that in these determinations for triglyceride in plasma, the reagent used was the reagent described in Example 2 above, and 3 μl samples were tested. Results are shown graphically in FIG. 7.

B. The procedure described in Example 6(A) was repeated except that instead of using plasma samples, 5 μl whole blood samples were used to determine total triglycerides, and therefore the substances removed by the washing procedure included red blood cells and hemoglobin as in Example 5(C). Also, the hematocrit values were measured and used to calculate correction factors. Results, following correction for hematocrit, are shown graphically in FIG. 8.

We claim:

1. A method for the quantitative determination of total cholesterol in a sample of whole blood, which method comprises:
   (a) contacting said sample with a quantity of particulate silica which is capable of selectively absorbing all lipoproteins in said sample;
   (b) separating the non-absorbed components of the sample from the silica with said lipoproteins absorbed thereon;
   (c) after step (b), releasing said lipoproteins absorbed to said silica; and
   (d) quantitatively determining the total cholesterol in said lipoproteins.

2. A method according to claim 1, wherein the separation in step (b) comprises the operation of washing the silica with water or an aqueous solution.

3. A method according to claim 1, wherein the silica is fumed silica.

4. A method according to claim 1, wherein said silica is employed in an amount sufficient to absorb the entire sample and the separation in step (b) consists of washing the silica with water or an aqueous solution.

5. A method according to claim 1, wherein the particulate silica is permanently attached to a solid inert carrier.

6. A method according to claim 5, wherein said solid inert carrier has at least a part of its surface coated with a layer of said particulate silica.

7. A method according to claim 6, wherein said solid inert carrier is a glass plate or rod.

8. A method for the quantitative determination of total cholesterol in a sample of whole blood, said method comprising:
   (a) contacting said sample with particulate silica capable of selectively absorbing all lipoproteins in said sample;
   (b) separating the non-absorbed components of the sample from the absorbed lipoproteins by washing the silica with water or an aqueous solution;
   (c) incubating the silica having said lipoprotein absorbed thereon with a reagent solution releasing said lipoprotein absorbed on said silica for determining cholesterol in said released lipoprotein by an enzymatic-colorimetric reaction;
   (d) removing the silica from the liquid incubation mixture; and
   (e) evaluating the intensity of the color generated in said liquid mixture by said enzymatic-colorimetric reaction and comparing the intensity with one or more standards of said lipoprotein component so as to determine the total cholesterol in said lipoproteins.

9. A method according to claim 8, wherein the evaluation of the color intensity in step (e) is carried out by spectrophotometric measurement of the optical density of the liquid mixture at a suitable wavelength.

10. A method according to claim 9, wherein the value of the optical density is compared with a standard calibration curve.

* * * * *